United States Patent
Lamey

Patent Number: 5,666,962
Date of Patent: Sep. 16, 1997

[54] THERMOGRAPHY AS A METHOD OF MEASURING VIRAL ACTIVITY IN A HERPES LABIALIS INFECTION

[75] Inventor: Philip-John Lamey, Northern Ireland, United Kingdom

[73] Assignee: Warner-Lambert Company, Morris Plains, N.J.

[21] Appl. No.: 421,172

[22] Filed: Apr. 13, 1995

[51] Int. Cl.$^6$ .................................................. A61B 5/00
[52] U.S. Cl. ............................................................. 128/736
[58] Field of Search .................................. 128/736, 633, 128/653.1, 664

[56] References Cited

U.S. PATENT DOCUMENTS

| | | | |
|---|---|---|---|
| 4,428,382 | 1/1984 | Walsall | 128/736 |
| 5,286,488 | 2/1994 | Manikas et al. | 424/195.1 |
| 5,386,117 | 1/1995 | Piety et al. | 250/330 |

OTHER PUBLICATIONS

American Journal of the Medical Sciences; Nov.—Dec. 1978, vol. 276, No. 3, pp. 319–323.

Primary Examiner—Max Hindenburg
Attorney, Agent, or Firm—Michael J. Atkins

[57] ABSTRACT

Disclosed is a non-invasive method of measuring the progress of viral activity in a mammalian herpes labialis episode, the method comprising the step of measuring the temperature of the symptomatic area of the herpes labialis episode during the episode. Also disclosed is a non-invasive method of preventing the clinical effects of a herpes labialis episode, the method comprising the steps of: measuring the temperature of the symptomatic area during the herpes labialis episode; and treating the herpes labialis episode with an effective amount of an antiviral agent sufficient to prevent a herpetic lesion. Further disclosed is a non-invasive method of confirming the efficacy of an antiviral agent in the treatment of a herpes labialis episode, the method comprising the steps of: standardizing a subject having a herpes labialis episode; measuring the temperature of the symptomatic area during the herpes labialis episode; treating the herpes labialis episode with an effective amount of an antiviral agent sufficient to prevent a herpetic lesion; and remeasuring the temperature of the previously symptomatic area of the subject after treatment with the antiviral agent. Still further described is a kit for preventing the progression of a herpes labialis episode to a herpetic lesion, the kit comprising: a thermographic sensing device; and an antiviral medication. The kit comprises a thermographic sensing devise and an antiviral medication.

25 Claims, 4 Drawing Sheets

FIG-3 CHANGE IN THERMOGRAPHIC AREA – SUBJECT 3

THERMOGRAPHY AS A METHOD OF MEASURING VIRAL ACTIVITY IN A HERPES LABIALIS INFECTION

FIELD OF INVENTION

The present invention is directed to thermographic imaging as a tool to measure the progress of viral activity in a herpes labialis episode. Thermographic imaging can also be used as a tool to prevent the clinical effects of a herpes labialis episode. Thermographic imaging can further be used to confirm the efficacy of an antiviral agent in the treatment of a herpes labialis episode. The present invention is further directed to a diagnostic kit to quantify a herpes labialis episode in terms of the heat emitted throughout the prodromal stage of an episode and provide an antiviral agent or medication to prevent the clinical symptoms of the episode.

BACKGROUND OF INVENTION

Recurrent herpes labialis is a common condition and the most common clinical manifestation of herpes simplex virus infection. Although normally self limiting, the disease state is both painful and socially and psychologically debilitating. Serologic studies have indicated that between 50% and 100% of the population have had primary contact with the herpes simplex virus by adulthood. Herpes labialis follows the primary infection usually by a number of years, but only in a proportion of those who had the primary infection. Numerous precipitating factors are recognized as casually related to episodes of herpes labialis including cold weather, sunlight, trauma, stress and menstruation.

Between attacks of herpes labialis, the virus lies dormant in nerve ganglion supplying the affected or symptomatic area. Following reactivation, the virus travels along the nerve to the skin. Once the virus reaches the skin, it replicates and causes an eruption or lesion commonly known as a cold sore.

The development of herpes labialis episodes are well recognized and can be characterized in four stages. The initial stage is a prodromal period lasting for a matter of hours to one to two days. The skin tingles and itches but no cold sore appears. In the next stage ("blister stage"), painful fluid filled blisters appear, which develop at the mucocutaneous junction of the lips. The duration of this stage is variable per individual, but normally lasts about two to five days. In the following stage ("open sore stage"), the blisters rupture and form weeping ulcers. Finally, in the last stage ("scabbed lesion stage"), the blisters dry out and crust over to form a scab. The entire episode with complete resolution of the condition takes seven to fourteen days.

Medical treatment of a herpes labialis episode is currently available. Application of an antiviral agent such as acyclovir heals cold sores. Acyclovir is absorbed through the skin's surface to prevent viral replication. If used at the prodromal (tingle) stage, topical application of acyclovir can prevent the cold sore from appearing.

While the prodromal stage of a herpes labialis episode is characterized by a tingling sensation, recognition of the prodromal stage by this sensation in the symptomatic area is subjective and limited to the individual infected. Further, recognition of the prodromal stage is difficult to quantify. The study of herpes labialis episode has previously been based on subjective clinical parameters such as pruritus and burning. The lack of means to recognize in a large audience, and to quantify repeatedly and accurately the prodromal stage of herpes labialis episode makes it difficult to document case where herpes labialis blisters has been prevented by treatment with antiviral agents such as acyclovir.

It can be understood that if one were to accurately and repeatedly quantify the progress of recurrent herpetic labialis episodes, the prevention of herpes labialis by treatment with an antiviral agent can be documented. What is demanded is a new non-invasive method of assessing the progress of the virus that results in the herpes labialis episodes. Such a technique complements more traditional methods of studying herpes labialis, such as by virus isolation and culture.

SUMMARY

It is an object of the invention to provide new and useful non-invasive methods of assessing and mapping a herpes labialis episode.

It is also an object of the invention to provide new and useful methods of measuring vital activity in a herpes labialis episode, particularly in the subclinical prodromal stage.

It is another object of the invention to provide new and useful methods of accurately and repeatedly preventing a herpes labialis episode by treatment with an antiviral agent.

It is yet another object of the invention to provide new and useful methods of confirming the existence of a prodrome, and thus documenting the prevention of a herpes labialis episode treated with an antiviral agent.

The invention achieves some of these objects by employing a thermographic to measure the progress of viral activities in herpes labialis episodes, particularly in the subclinical prodromal stage. Thermography of an infected area demonstrates a significant subclinical localized elevation in temperature at the site where prodromal symptoms are perceived. Treatment with an antiviral agent at this point generally prevents the developing lesion. After a successful treatment, the infected individual registers thermographically normal. Antiviral agents are defined to be those compounds or compositions which act in some degree to inhibit the replication of a virus, preferably the herpes simplex virus.

This technique provides a quick mechanism for assessing drugs for example antiviral agents used to treat cold sores. It also is capable of providing regulatory authorities such as the Food & Drug Administration with data to support and document the efficacy of antiviral agents in preventing the development of herpes lesions.

Other benefits and advantages of the present invention will become readily apparent to those skilled in the art from the following detailed description of the invention, the drawings and the appended claims.

DETAILED DESCRIPTION OF THE INVENTION

The present invention is directed in one embodiment to a non-invasive method of measuring the progress of viral activity in a mammalian herpes labialis episode, the method comprising the steps of: (a) optionally standardizing a subject having a herpes labialis episode; and (b) measuring the temperature of the symptomatic area of the herpes labialis episode during one or more of the four stages of the episode. More specifically, as indicated above, the present invention is directed to thermographic imaging as a tool to measure the progress of viral activity in a herpes labialis episode. In the preferred embodiment, temperature changes accompanying the various stages of a herpes labialis episode, such as the prodromal stage, blister stage, open sore stage and scabbed lesion stage are determined to measure viral activity. Measurement of the temperature changes is accomplished by suitable means for thermographically sensing the radiation of at least a portion of the herpes labialis episode, such as a thermographic imaging system.

In certain instances it is also important to measure the temperature of a subject before and after the occurence of a herpes labialis episode. Thus, in one embodiment of the present invention, the non-invasive method of measuring the progress of viral activity in a herpes labialis episode further comprises the steps of: (a) measuring the temperature of an area of a subject prior to the occurrence of a herpes labialis episode: and (b) comparing the temperatures measured prior to and during the herpes labialis episode. In another embodiment of the present invention, the non-invasive method of measuring the viral activity in a herpes labialis episode further comprises the steps of: (a) measuring the temperature of an area of a subject after the occurrence of a herpes labialis episode; and (b) comparing the temperatures measured during and after the herpes labialis episode.

Any thermographic imaging systems known to those of skill in the art may be employed in the present invention. Thermographic imaging systems which are known to those of skill in the art include electric skin resistance, calorimetric tests, plethysmography and thermocoupling. Thermographic imaging systems include those disclosed explicitly or by reference in U.S. Pat. Nos. 5,375,603, 5,386,117 and 5,010,608. Preferably, an infra-red thermographic imaging system is employed in the present invention.

In the preferred embodiment of the present invention, infra-red sensing devices are employed to evaluate and record temperature changes in subjects due to herpes labialis episodes. Due to technical developments in sensitive detectors and image analysis systems, techniques such as infra-red thermography have reached a very high standard of performance and are well known to those skilled in the art.

Infra-red thermography is defined as the recording of the temperature of a body by means of infra-red radiation emitted by the surface of that body at wavelengths between 0.8 µm and 1 mm. The human body is an almost perfect emitter of infra-red radiation, with maximal emission around 8–10 µm wavelength. As homeotherms, humans continually generate heat; this heat production can be categorized as minimal, food inducible and regulatory, which relates to basal metabolism, A.T.P. breakdown with food conversion and enhanced muscular activity or non-shivering thermogenesis, respectively. This heat must be released by the body to the surroundings so that the core body temperature stability is maintained.

The transfer of heat to the surroundings occurs via four different mechanisms, (1) conduction which is the exchange of heat between adjacent spatially fixed particles, (2) convection which is the transport of heat by moving particles namely blood and/or air currents, (3) evaporation which employs heat transfer associated with the transition from the liquid to gaseous phase and (4) radiation which is the radiant exchange of heat without a material heat carrier. Therefore in steady state conditions, the heat produced within the body and heat loss to the surroundings are in equilibrium. Within stable ambient conditions of 18°–25° C., with no convective air currents or external radiation sources, the principal mechanism to achieve thermal equilibrium between a body and its environment is via radiation. However, it must always be noted that skin temperature is not constant and is affected by a number of variables including environmental conditions, skin vasculature, circadian rhythms, physical workload, metabolic state, drug effects and the individual's psychological state. To minimize these variations, a subject can be standardized by eliminating these conditions before proceeding with a thermographic recording. For example, a subject may be asked to refrain from eating, smoking and strenuous physical exercise before examination, and any facial cosmetics may be removed.

It is possible to obtain information about the heat being emitted in and around a herpes labialis episode as a means for dynamically measuring, both quantitatively and qualitatively, the progress of disease activity in herpes labialis episodes in mammals including humans. If infra-red thermographic imaging is used, the information can be color-coded. Measurement of the progress of the herpes labialis episode development in terms of the heat emitted is associated with consistently increased temperature above background. For example, an infra-red sensing device can provide a map or profile of surface temperatures throughout the herpetic area during an episode. These temperatures can be depicted by assigning different colors of the spectrum to predetermined temperature ranges. This graphic depiction of temperature throughout the herpetic area can be correlated to the various stages of the herpes labialis episode, thus providing useful diagnostic and treatment information by having an accurate, reproducible and dynamic source of information about the progress of a herpes labialis episode. An informed decision about treatment, or the documentation of the prevention of a herpetic lesion can then be accomplished.

The means for dynamically measuring temperature changes in herpes labialis episodes described hereinafter is capable of providing a color-graphic or gray scale depiction at each stage of a herpes labialis episode. At each stage of the episode, and after a patient has been stabilized, images are displayed, recorded and/or stored. In one embodiment of the present invention, the results of the thermographic measurements are displayed in a written, electronic or visual format.

As noted above, a temperature sensing device, and preferably an infra-red sensing device, can be utilized as a non-invasive means for dynamically estimating temperature changes. In particular, an infra-red system produced by AGEMA Infra Red Systems (the AGEMA 900) can be customized to work well as a means for dynamically estimating temperature changes. The AGEMA 900 has heretofore typically not been used for this purpose; however, the apparatus can be adapted by techniques known to those skilled in the art to perform the desired function of estimating changes in temperature in a herpes labialis episode, and thus can be adapted for use in the methods of the present invention. This equipment optionally involves the use of a reflecting infra-red mirror, a zoom lens with a focusing device, an adaptor and a video recorder, a keyboard for entering identifying information, a computer with image enhancement capability, a stand for the mirror, a rolling cabinet for the other equipment, a power source suitable for the operating room, two color monitors and a means for changing the angle of the mirror remotely.

The methods of the present invention are as sensitive as more traditional methods of studying herpes labialis episodes, such as by virus isolation and culture, but have the advantage of demonstrating changes in the infective and related areas by a dynamic, temperature dependent method rather than relying solely on invasive techniques. Additionally, the methods of the present invention give more precise relative information from which decisions can be made on how to treat the episode, which if accomplished at an early stage can prevent the occurrence of the unsightly clinical stages of the disease.

In a preferred embodiment of the present invention, a means for dynamically estimating temperature changes is employed to demonstrate in color or gray scale and with on-line computer enhancement the temperature profile in the vicinity of the diseased area by utilizing certain predetermined color ranges. For example, it has been found that in accordance with the present invention, a ten color range over a five degree Centigrade range works well, each color then representing a one-half degree Centigrade temperature change. Resolution of the electronic infra-red thermographic sensing devices is of the order of magnitude of about 0.1° C.

The present invention is also directed to a non-invasive method of treating the clinical effects of a herpes labialis episode, the method comprising the steps of: (a) optionally standardizing a subject having a herpes labialis episode; (b) measuring the temperature of the symptomatic area during one or more of the four stages of the herpes labialis episode; and (c) treating the herpes labialis episode with an effective amount of an antiviral agent sufficient to prevent a herpetic lesion. More specifically, the increase in temperature of the affected area can be characterized by the infra-red emissions of a prodromal stage of a herpes labialis episode (in the range from about 1°–3° C. above background) and measured by use of a thermographic imaging system, and treated to prevent the clinical manifestations of the episode. Treatment can occur by the application of an antiviral agent such as acyclovir.

Although the disclosure of the invention thus far is directed to applications of the present invention for herpes labialis episodes arising around the lips, it will be readily apparent to those skilled in the art that the methods of the present invention are also applicable to other areas of the body, such as the genital area, fingers (herpetic whitlow) and, more seriously, ocular infections (keratitis).

As indicated above, in certain instances it is also important to measure the temperature of a subject before and after the occurence of a herpes labialis episode. Thus, in one embodiment of the present invention, the method of preventing the clinical effects of a herpes labialis episode further comprises the steps of: (a) measuring the temperature of a symptomatic area of the subject prior to the occurrence of the herpes labialis episode; and (b) comparing the temperatures measured prior to and during the herpes labialis episode. In another embodiment of the present invention, the method of preventing the clinical effects of a herpes labialis episode further comprises the steps of: (a) measuring the temperature of an area of the subject after treatment with the antiviral agent; and (b) comparing the temperatures measured during the herpes labialis episode and after treatment with the antiviral agent.

Preferred antiviral agents are the compounds acyclovir and famcyclovir, most preferably acyclovir delivered in a composition along with certain known pharmaceutically acceptable carriers and excipients (ZOVIRAX® or ACTIVIR®). Nevertheless, it should be understood that other effective antiviral agents known to those of skill in the art may be employed in the present invention. Also, regardless of the route of administration selected, the antiviral agents may be formulated into pharmaceutically acceptable dosage forms by conventional methods known to the pharmaceutical art.

An effective, but nontoxic quantity of the antiviral agent is employed in the treatment. The amount of antiviral agent to treat the prodromal stage will depend upon numerous factors such as the antiviral agent, particular application and the individual receiving treatment. Preferably, the pharmaceutical preparation of at least one antiviral agent is in unit dosage form. The quantity of active compound in a unit dose of preparation may be varied or adjusted from about 1 mg to 500 mg, preferably from about 1 to 200 mg. As an example, 5% w/w acyclovir in water miscible cream base is applied 5 times a day for 5 days. The pharmaceutical compositions can, if desired, also contain other compatible therapeutic agents.

The present invention is additionally directed to a non-invasive method of confirming the efficacy of an antiviral agent in the treatment of a herpes labialis episode, the method comprising the steps of: (a) standardizing a subject in the prodromal or earlier a herpes labialis episode; (b) measuring the temperature of the symptomatic area during the herpes labialis episode; (c) treating the herpes labialis episode with an amount of an antiviral agent sufficient to prevent a herpetic lesion; and (d) remeasuring the temperature of the symptomatic area of the subject after treatment with the antiviral agent. More specifically, after standardizing a subject, the prodromal stage of a herpes labialis episode is measured thermographically to confirm its presence, the infected area is treated with an antiviral agent such as acyclovir, and the area is later remeasured thermographically to confirm the efficacy of the antiviral agent in treating the herpes labialis episode; in other words, the herpes labialis episode does not progress from the prodromal stage to the herpetic lesion stage and the temperature returns to baseline. The temperature of the previously symptomatic area is remeasured from about 2 to 10 days after treatment.

The application of thermographic imaging to herpes labialis episodes is important as it allows, for the first time, objective measurement, quantitatively and qualitatively, of the subclinical phase of an infective process. There is evidence that acyclovir reduces the healing time of herpes labialis lesions, but probably more importantly has been claimed to prevent herpes labialis lesion development in around 40% of cases treated early. Using thermographic imaging the subclinical phase can now be quantified and be shown to produce clinical and thermographic resolution if treated early enough with acyclovir.

As indicated above, the present invention is further directed to a kit for preventing the progression of the subclinical effects to the clinical effects of a herpes labialis episode, the kit comprising (a) a thermographic sensing device; and (b) an antiviral agent. The diagnostic kit measures a herpes labialis episode in terms of the heat emitted throughout the prodromal stage of an episode and provides an antiviral agent to treat and prevent the clinical symptoms of the episode.

The thermographic sensing device assesses the temperature changes associated with the prodromal stage of a herpes labialis episode. This change in temperature is a signal to begin treatment with an antiviral agent to prevent progression of the episode to the stages where clinical effects such as cold sores are manifest. The preferred antiviral agent is acyclovir.

The following examples are provided to illustrate specific embodiments of the methods and kits of the present invention. They are to serve as illustrations only, and it is realized that minor changes and modifications are possible and should not be regarded as falling outside the spirit and scope of the present invention as later defined by the appended claims.

EXAMPLES

Example 1

A study was carried out to measure the progress of disease activity in a mammalian herpes labialis episode. The study measured recurrent herpetic lesions in terms of the heat emitted throughout the stages of untreated herpes labialis episodes. The patients were all staff members of the Royal Victoria Hospital who suffered from recurrent herpes labialis. All were requested to report to the School of Clinical Dentistry for enrollment in the trial. Ten patients were studied after giving informed consent. All were female, means age 25±5 years and all underwent the same study protocol.

Each patient reported at the onset of the prodrome, usually within one to two hours. They were assessed by the clinician for (a) stage of lesion recorded as prodrome, vesicle or crust and (b) clinical area of lesion ($mm^2$). For each active episode, swabs were taken from recently ruptured vesicles and placed in viral transport medial. Virus isolation and culture were confirmed using the HEP-2 technique. The infrared thermographic imaging system utilized was the Agema 900 thermovision system (Agema Infrared Systems AB, Danderyd, Sweden). All patients were requested to refrain from eating, smoking and strenuous physical exercise before examination. Facial cosmetics were removed and lesions were not treated. On arrival, patients were thermally stabilized in a room with a constant environment (20° C.±1° C.) for 20 minutes. No radiation sources were present and air convection was minimized. Subsequent visits were requested to be at a similar time of day.

For thermographic assessment, two images were recorded and stored. The first image was a facial thermogram of a subclinical developing prodromal herpes labialis lesion at a focal length of 0.5 meters. At least in one instance, the lesion site was right of center on the upper lip. The localized increase in temperature was seen as a lighter shade. The second image was a facial thermogram of developing prodromal lesion site (<1 hour after patient recognition). The image was a close-up of the lesion using a macro lens set at a focal distance of 0.05 m. At least in one instance, the position of the lesion was left of center on the lower lip. An intense white, "hot," area to the right of the lesion on this image, corresponded to naturally warmer areas at the lip junctures these were considered normal thermal patterns for these areas.

These two thermograms were used for quantitative assessment. Several parameters were recorded using the system software; firstly, the maximum temperature within the symptomatic region, and secondly, the background temperature, i.e. normal tissue temperature, and finally, the thermally active area in $mm^2$. All patients underwent the same study protocol and were assessed daily until complete clinical and thermographic resolution. Each patient attended the clinic, for thermal assessment of their developing lesion, during the first eight hours of their next two subsequent prodromal stages. This allowed each patients thermal variability between active episodes to be observed. Fisher's Exact Test was used for paired comparisons. P-values of <0.05 were considered significant.

All patients successfully reported for clinical and thermographic assessment from the prodromal stage to resolution. Viral culture was positive for Herpes simplex Type 1 in all patients. In the prodromal phase there was an increase in temperature over the symptomatic area of 1.6° C.±0.5° C. with the mean duration of the prodromal phase extending from 7.25±3.4 hours. Thermographically the prodromal phase was demonstrated by the two facial thermograms.

Thermograms of vesicular herpes labialis lesions in the subjects were then performed. A temperature increase was maintained throughout the vesicle phase, however, a difference was noted that the central area of the vesicle became colder, presumably due to the insulating effect of the fluid. At least in one instance, a lesion on the center of the upper lip of the subject could be seen as a "lighter," warmer area with a "darker," colder center. This colder area was due to the fluid filled vesicles.

Thermograms of herpes labialis episodes in the crusting stage in the subjects were then performed. During crusting, the central area became even colder due to separation of the surface epithelium. The crust was seen as a central darker area within an area of increased temperature.

Figure 1:
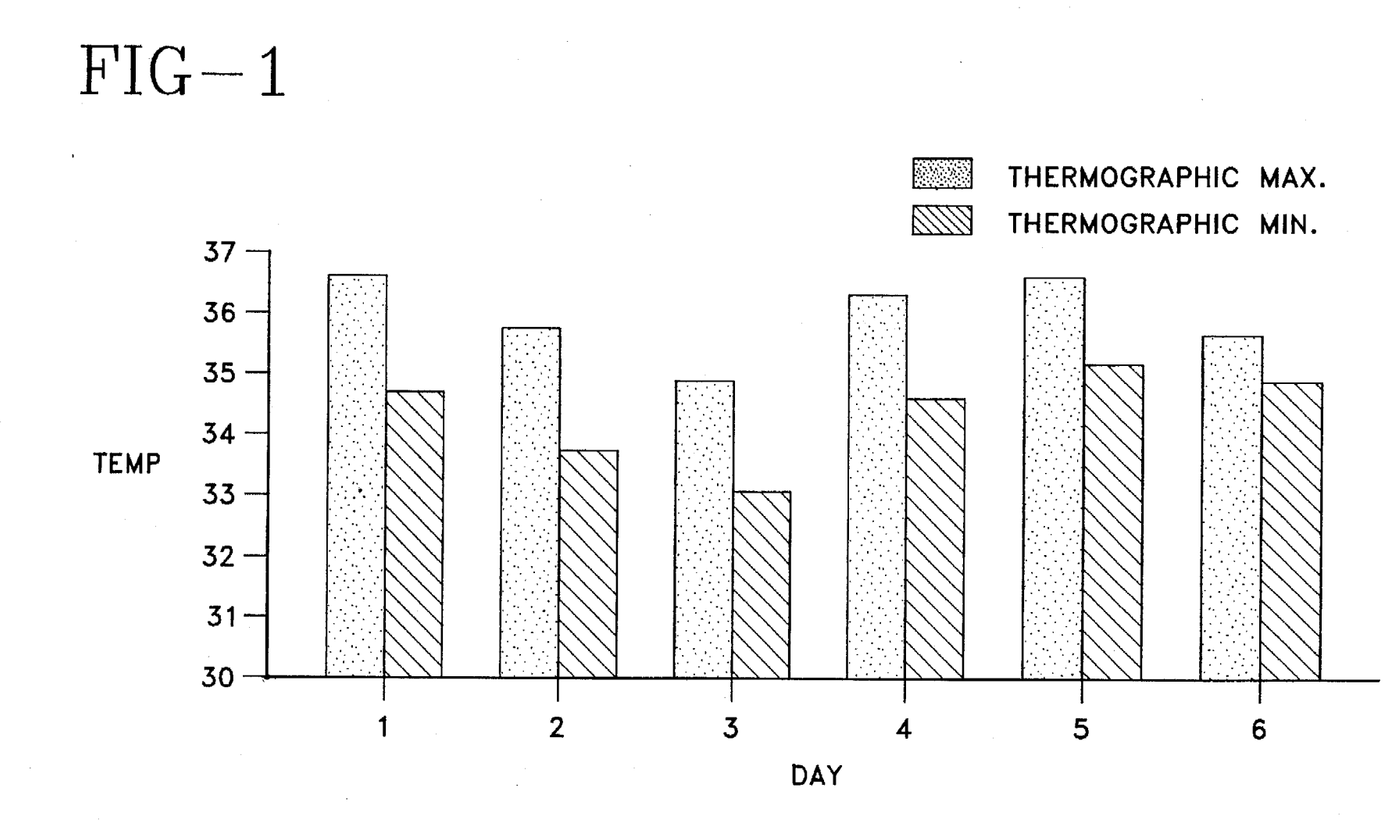
FIG. 1. Bar chart illustrating the mean maximum (active) and minimum (background) temperatures for ten patients' active episode of recurrent herpes labialis from day one through to day six.

The mean maximum and minimum temperatures for the ten patients' active lesions from day one through to day six are shown in FIG. 1. These are the mean temperatures recorded within the active lesion areas. As the condition progresses through the different stages, the difference in temperature ($\Delta T°$) was reduced, though even after day six a small $\Delta T°$ of approximately 0.5° C., was still measurable. Throughout this period the lesions showed an increase in temperature above that of the surrounding skin. There was a reduction in the temperature through days two and three; however, the differences ($\Delta T°$) between maximum temperature and background were not reduced (Table I).

TABLE I

MEAN MAXIMUM AND BACKGROUND TEMPERATURES FOR TEN PATIENTS OVER SIX DAYS

| Day | Mean Maximum Temperature (°C.) | Standard Deviation | Mean Background Temperature (°C.) | Standard Deviation |
| --- | --- | --- | --- | --- |
| 1 | 35.72 | 1.12 | 34.1 | 0.86 |
| 2 | 35.00 | 1.68 | 33.2 | 1.70 |
| 3 | 34.20 | 1.67 | 32.6 | 1.62 |
| 4 | 35.57 | 0.66 | 34.0 | 0.67 |
| 5 | 35.73 | 0.76 | 34.5 | 0.50 |
| 6 | 34.95 | 0.21 | 34.3 | 1.00 |

Figure 2:
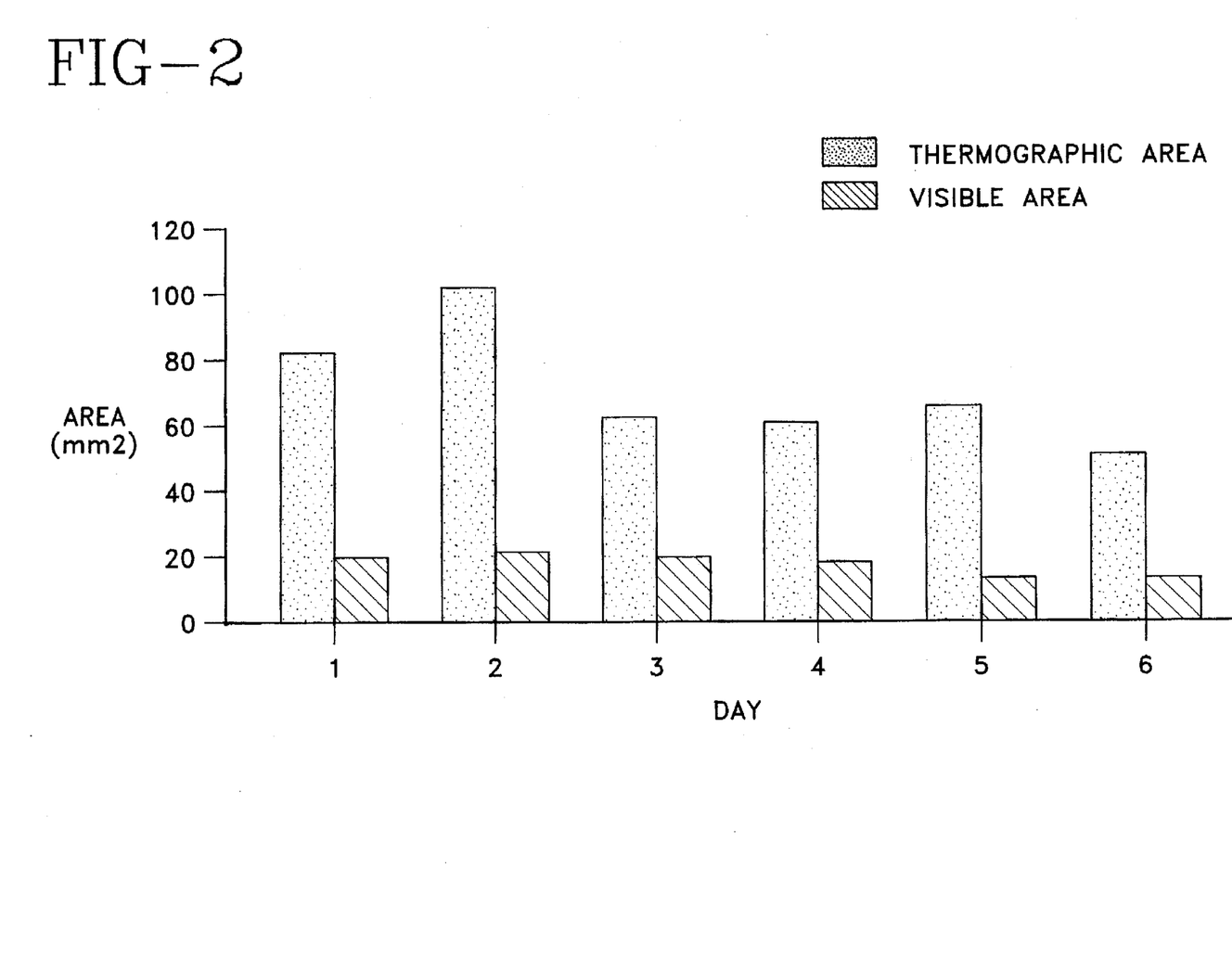
FIG. 2. Differences between the thermographically mean active areas ($mm^2$) and the observed mean clinical areas ($mm^2$) for the ten patients from day one through to day six.

Following the vesicle phase, which had a mean duration of 2.3 days ±1.2 days, the temperature differences ($\Delta T°$) were decreased, but still measurable at day six. It normally took eight to ten days for the condition to be thermographically normal, with the mean crusting phase being 6.3 days ±4.2 days. The second measured parameter was the thermographically visible area of the lesion. The difference between the clinical area and thermographic area was termed $\Delta A mm^2$. FIG. 2 illustrates the difference in measured areas, clinically and thermographically. Here large differences were seen between the two methods. Firstly, the thermographically active area was always far greater than that observed clinically (especially during the prodromal phase). The clinically evident area was relatively constant, with a slight reduction towards days five and six as the crusting stage resolves. However, even at day six the thermographically active area was still approximately twice as large as the clinical area of the lesion.

Figure 3:
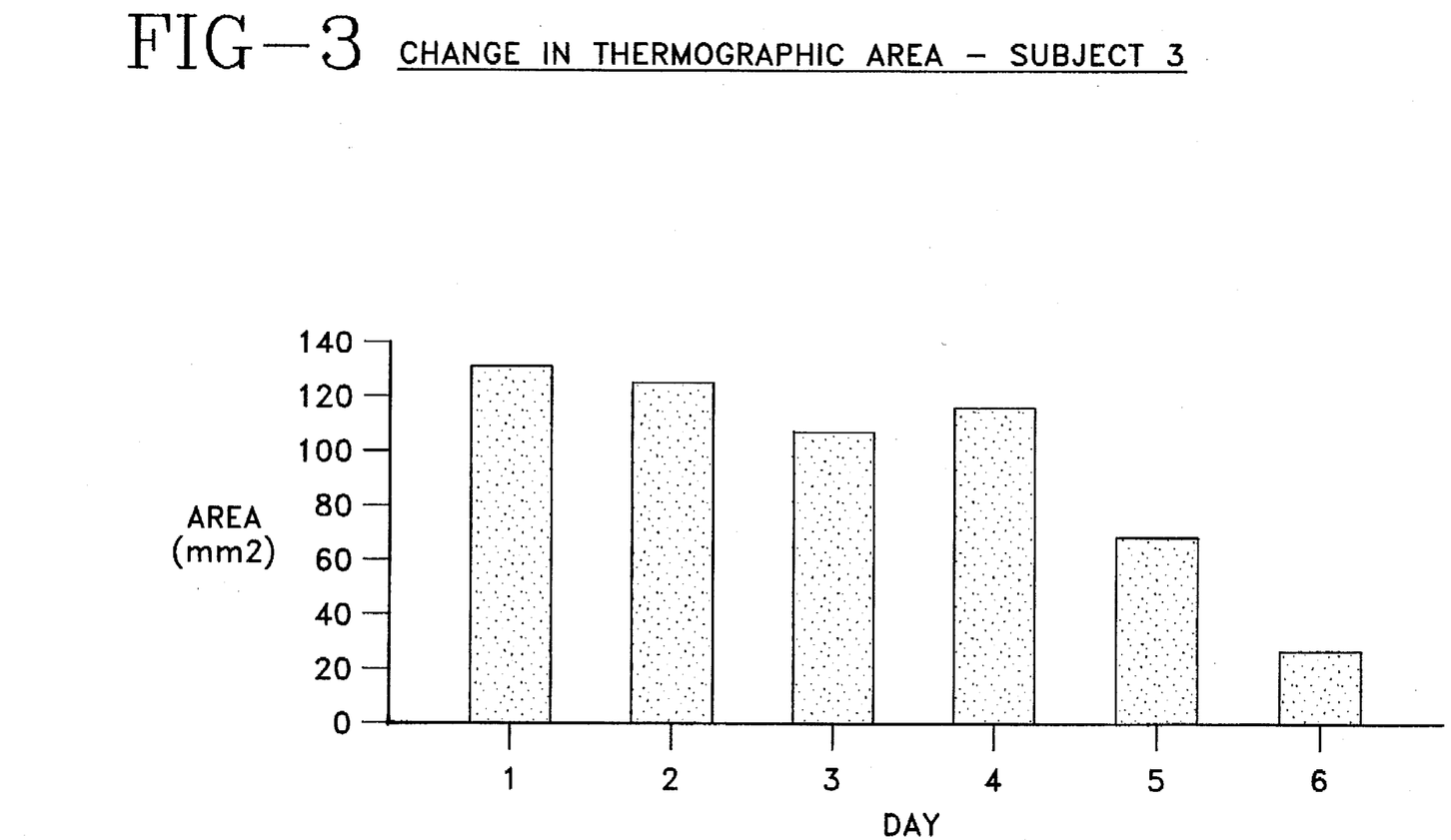
FIG. 3. Bar chart illustrating the differences in the thermographically active area between patient three and five demonstrating inter-patient variability of results.
Figure 3A:
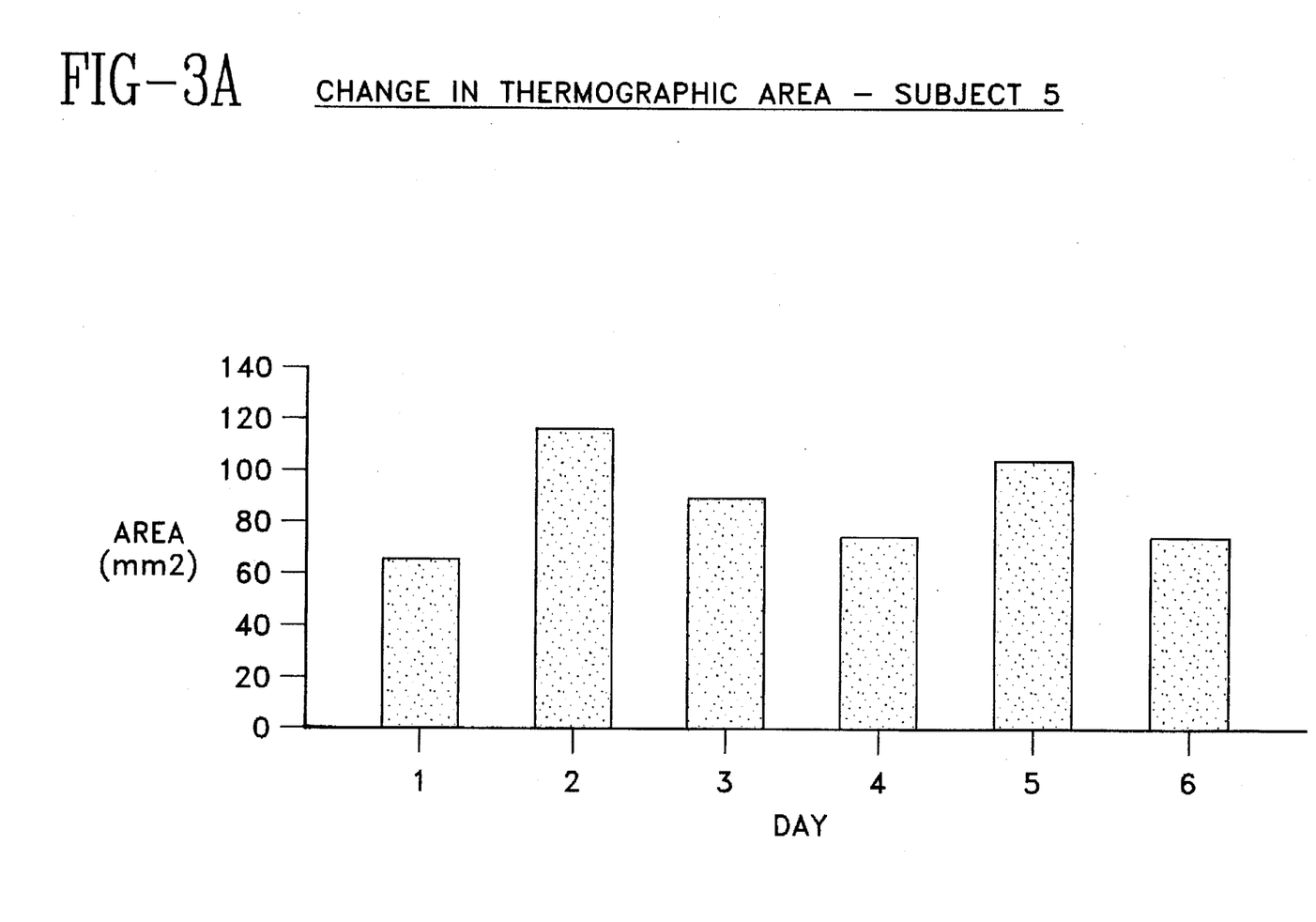

Finally, the reproducibility of thermal radiance between individual episodes of herpes labialis episode for the ten patients was undertaken due to the variability in the data when considered with respect to inter-patient comparison. FIG. 3 illustrates the differences observed for the parameter of thermographic area as observed between subjects three and five. These differences in area development, when studied collectively, may mask small but significant changes. Therefore, patients returned for thermal assessment of the prodromal stage of their next two active episodes, the results of which are shown in Table II. All patients exhibited an increase in temperature for each episode. Each patient's mean temperature change for the three readings is shown, all were 1° C. or more above background. However, the standard deviation about the mean illustrated a marked constancy per individual, with a maximum deviation of only 0.26 of a degree.

TABLE II

MEAN LOCALIZED TEMPERATURE INCREASE FOR TEN SUBJECTS OVER THE PRODROMAL STAGE OF THREE ACTIVE LESIONS
Prodromal $\Delta T°C$. Over 3 Active Episodes

| Patient No. | $X\Delta T°C$. | ±SD |
|---|---|---|
| 1 | 1.63 | 0.20 |
| 2 | 1.40 | 0.20 |
| 3 | 1.70 | 0.14 |
| 4 | 1.30 | 0.14 |
| 5 | 1.40 | 0.26 |
| 6 | 1.37 | 0.20 |
| 7 | 1.15 | 0.07 |
| 8 | 1.50 | 0.20 |
| 9 | 1.70 | 0.15 |
| 10 | 1.10 | 0.10 |

The study of herpes labialis episode has previously been based on subjective clinical parameters such as reduction in pruritus and burning. This thermographic study allowed the measurement of the herpetic lesion development in terms of the heat emitted and its association with consistently increased temperature above background level. This point is illustrated in Table II, showing the change in temperature for the ten patients' active lesions from day one through to day six. All ten patients exhibited a localized increase in temperature on day one and collectively the mean $\Delta T°$ was 1.6° C.±0.15° C. However, the timing of thermal assessment was important, since the evolving prodrome was a dynamic process resulting in an increase in temperature with time. Once vesicle information began, the cooler areas associated with this delineated active site reduced the overall increase in $\Delta T°$. This meant that any collective assessment had to be time-matched so that prodromal development could be assessed at a similar stage. The reduction in temperature at the center of the developing lesion from day one through to day three could probably be attributed to the development of the vesicle stage. Two factors could have been involved; firstly, the fluid within the vesicles may have had an insulatory effect on the heat irradiated; secondly, when the vesicles weep, the evaporation of the fluid from the skin may have caused a reduction in the temperature site. What should be emphasized was the reduction in the $\Delta T°$ between day three through to day six. This gradual reduction signified the reduction in the inflammatory response and hence indicated that the healing process was progressing. When considering the entire herpetic lesion, the thermographically active area was significantly greater than that observed clinically, but whether or not active virus was present throughout this area was unproven. Nevertheless, from day three through to day six, the difference between the clinical area seen and that observed thermographically ($\Delta A mm^2$) was reduced throughout this time period in an analogous way to $\Delta T^{602}$. However, this larger thermographically active area was obviously related to viral activity and could have implications for topical delivery of anti-viral agents.

There was some inter-patient variability in the parameters measured as can be seen in FIG. 3. To test the reproducibility of $\Delta T^{602}$ and/or $\Delta A mm^2$, each patient returned during two subsequent prodromal phases. Since all patients were examined within four to six hours of recognizing the prodromal symptoms, then the time matching problem was addressed. Thus, Table II illustrates that such variations could be minimized, which would be an important consideration therapeutically. In this context, identification and quantification of the subclinical prodromal phase was of paramount importance.

Example 2

A study was carried out to assess the intra-patient variability of thermal radiance during the untreated prodromal stage of the active episode as measured by infrared thermography. Ten volunteers with histories of a herpes labialis episode were accepted for the trial after giving informal consent. All volunteers were assessed immediately on development of a suspected active episode and underwent the same study protocol for three untreated episodes. All were examined thermographically within a stable environment, 20°±1° C. with minimized air convection and no radiation sources. After a 20 minute acclimatization period, thermographic images were taken at 2 focal lengths, 0.5 m and 0.05 m. These allowed for orientation assessment of symmetry and detailed analysis. Lesions were followed to healing for clinical evaluation and virus isolation for confirmation of disease state. All volunteers showed consistent increases in temperature during the prodromal phase. Mean temperature for 10 volunteers over 3 active episodes=1.42° C. above normal. Variability within patients for 3 episodes ranged only from 0.1° C. to 0.26° C. about mean temperature increase. A consistent increase in temperature during the prodromal stage of recurrent untreated herpes labialis was a quantifiable factor as measured by infra-red thermography.

Example 3

A thirty year old hospital manager came to the Oral Medicine Clinic complaining of a tingling and burning sensation of his upper lip. The abnormal sensations had begun three hours earlier and the patient recognized the symptoms as being typical of the prodromal stage of herpes labialis as he had suffered from this condition intermittently for the previous fourteen years. Prior visits to his general medical practitioner had confirmed previous episodes of the condition as being due to herpes simplex Type 1 using HEP-2 culture techniques.

On examination at the clinic the patient appeared entirely healthy, there were no skin changes over the symptomatic area and no treatment had yet been undertaken. Using thermography, the patient was diagnosed as being in the prodromal phase of another episode of recurrent herpes labialis.

As described in Example 1, the prodromal phase of herpes labialis can be detected using electronic infrared thermography. The patient underwent thermographic imaging. An AGEMA 900 series system was used. A first thermal pattern was observed on initial patient attendance at the clinic. Different colors represented different temperatures. The subclinical lesion was observed as a light "orange". Its position was on the upper lip below the nose. Other facial features visible were the nose, which was dark due to it being colder than other facial structures and the juncture of the lips which was a lighter/warmer line which arched across the thermogram. This was a half face thermogram set at a focal distance of 0.5 m from the surface of interest. A localized increase in temperature on the symptomatic site was evident and was of 1.7° C. magnitude.

A second thermal pattern was also observed on initial patient attendance at the clinic. This thermogram of the lesion was measured at 0.05 m using an AGEMA 900 series system. The position of the prodromal lesion was seen as a "yellow" area in the center of the thermogram. This close-up thermogram was used for more detailed analysis. Area of thermal involvement, maximum temperature and statistical average temperature were all calculated using this focal length thermogram.

The patient had previously had herpes simplex Type 1 isolated from untreated lesions on the same site thereby confirming the diagnosis of herpes labialis. Imaging of the prodromal phase of herpes labialis lesions showed a temperature rise of 1.42° C.±0.2 which is typical of the prodromal phase. This temperature rise occurred early i.e. within an hour of the prodromal phase developing.

Following imaging the patient was prescribed acyclovir cream (2 g) (ZOVIRAX®) and instructed to apply the cream over the termographicaily affected area five times a day for five days. Review was arranged for two days later. At that time the patient was asymptomatic and repeat thermographic imaging was undertaken. When compared to the imaging taken prior to treatment, the difference in thermal pattern was easily appreciated. The facial appearance of the patient on this occasion was thermographically normal. The initially elevated temperature at the prodromal site had returned to background levels. More specifically, there was no measurable change in temperature at the site of involvement. On clinical examination no visible signs of the lesion were evident. Clinically and thermographically the previously symptomatic area was normal.

What is claimed:

1. A non-invasive method of measuring the progress of viral activity in a mammalian herpes labialis episode, the method comprising the step of measuring an increase in the temperature of the symptomatic area of the herpes labialis episode in the range from about 1°–3° C. above background during one or more of the four stages of the episode.

2. The method of claim 1, wherein the temperature of at least the prodromal stage of a herpes labialis episode is measured.

3. The method of claim 1, wherein the temperature of at least the blister stage of the herpes labialis episode is measured.

4. The method of claim 1, wherein the temperature of at least the open sore stage of the herpes labialis episode is measured.

5. The method of claim 1, wherein the temperature of at least the scabbed lesion stage of the herpes labialis episode is measured.

6. The method of claim 1, further comprising the steps of:

(a) measuring the temperature of the symptomatic area of a subject prior to the onset of a herpes labialis episode; and (b) comparing the temperatures measured prior to and during the onset of the herpes labialis episode.

7. The method of claim 1, further comprising the steps of:

(a) measuring the temperature of a symptomatic area of a subject after the occurrence of a herpes labialis episode; and (b) comparing the temperatures measured during and after the herpes labialis episode.

8. The method of claim 1, wherein the step of measuring the temperature comprises the use of a means for thermographically sensing the infra-red radiation of at least a portion of the herpes labialis episode.

9. The method of claim 1, wherein the step of measuring the temperature comprises use of an infra-red thermographic imaging system.

10. The method of claim 1, further comprising the step of standardizing a subject having a herpes labialis episode.

11. A non-invasive method of preventing the clinical effects of a herpes labialis episode, the method comprising the steps of:

(a) measuring the temperature of the symptomatic area during at least one stage of the herpes labialis episode; and (b) treating the symptomatic area during the herpes labialis episode with an amount of an antiviral agent sufficient to prevent a herpetic lesion when an increase in temperature is measured in the range from about 1°–3° C. above background.

12. The method of claim 11, wherein the temperature of the prodromal stage of a herpes labialis episode is measured.

13. The method of claim 11, further comprising the steps of:

(a) measuring the temperature of a symptomatic area of the subject prior to the onset of the herpes labialis episode; and (b) comparing the temperatures measured prior to and during the prodromal stage of the herpes labialis episode.

14. The method of claim 11, further comprising the steps of:

(a) measuring the temperature of a symptomatic area of the subject after treatment with the antiviral agent; and (b) comparing the temperatures measured during the herpes labialis episode and after treatment with the antiviral agent.

15. The method of claim 11, wherein the step of measuring the temperature comprises a means for thermographically sensing the infra-red radiation of at least a portion of the herpes labialis episode.

16. The method of claim 11, wherein the step of measuring the temperature comprises use of an infra-red thermographic imaging system.

17. The method of claim 11, wherein the antiviral agent is acyclovir.

18. The method of claim 11, further comprising the step of standardizing a subject having a herpes labialis episode.

19. A non-invasive method of confirming the efficacy of an antiviral agent in the treatment of a herpes labialis episode, the method comprising the steps of:

(a) standardizing a subject in the prodromal or earlier stage of a herpes labialis episode;

(b) measuring the temperature of the symptomatic area;

(c) treating the symptomatic area during the herpes labialis episode with an amount of an antiviral agent sufficient to prevent a herpetic lesion when an increase in temperature is measured in the range from about 1°–3° C. above background; and (d) remeasuring the temperature of the symptomatic area of the subject for about 2–10 days after treatment with the antiviral agent.

20. The method of claim 19, further comprising the step of comparing the temperatures measured during the herpes labialis episode and after treatment with the antiviral agent.

21. The method of claim 19, wherein the temperature of the prodromal stage of a herpes labialis episode is measured prior to treatment.

22. The method of claim 19, further comprising the steps of:

(a) measuring the temperature of an area of the subject prior to the occurrence of the herpes labialis episode; and (b) comparing the temperatures measured prior to and during the prodromal stage of the herpes labialis episode.

23. The method of claim 19, wherein the step of measuring the temperature comprises a means for thermographically sensing the infra-red radiation of at least a portion of the herpes labialis episode.

24. The method of claim 19, wherein the step of measuring the temperature comprises use of an infra-red thermographic imaging system.

25. The method of claim 19, wherein the antiviral agent is acyclovir.

* * * * *